(12) United States Patent
Radicke

(10) Patent No.: US 9,453,803 B2
(45) Date of Patent: Sep. 27, 2016

(54) X-RAY RADIOGRAPHY SYSTEM FOR DIFFERENTIAL PHASE CONTRAST IMAGING OF AN OBJECT UNDER INVESTIGATION USING PHASE-STEPPING

(71) Applicant: Siemens Aktiengesellschaft, München (DE)

(72) Inventor: Marcus Radicke, Fürth (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 173 days.

(21) Appl. No.: 13/973,156

(22) Filed: Aug. 22, 2013

(65) Prior Publication Data

US 2015/0030126 A1  Jan. 29, 2015

(30) Foreign Application Priority Data

Jul. 23, 2013 (DE) .......................... 10 2013 214 393

(51) Int. Cl.
*A61B 6/00* (2006.01)
*G01N 23/04* (2006.01)
(Continued)

(52) U.S. Cl.
CPC ............... *G01N 23/04* (2013.01); *A61B 6/484* (2013.01); *H01J 35/14* (2013.01); *A61B 6/4035* (2013.01); *A61B 6/4233* (2013.01); *A61B 6/4291* (2013.01); *A61B 6/4441* (2013.01); *A61B 6/4458* (2013.01); *G01N 2223/064* (2013.01); *G01N 2223/316* (2013.01); *G21K 1/06* (2013.01); *G21K 2207/005* (2013.01)

(58) Field of Classification Search
CPC .. A61B 6/484; A61B 6/4035; A61B 6/4233; A61B 6/4291; A61B 6/4441; A61B 6/4458; G01N 23/04; G01N 2223/064; G01N 2223/316; G21K 1/06; G21K 2207/005; H01J 35/14
See application file for complete search history.

(56) References Cited

U.S. PATENT DOCUMENTS

| 7,500,784 | B2 | 3/2009 | Grebner |
| 8,284,894 | B2 | 10/2012 | Poorter |
| 2004/0022361 | A1* | 2/2004 | Lemaitre ..................... 378/138 |

(Continued)

FOREIGN PATENT DOCUMENTS

| DE | 10245676 B4 | 1/2008 |
| DE | 102010018715 A1 | 11/2011 |
| EP | 1803398 A1 | 7/2007 |

OTHER PUBLICATIONS

Weitkamp et al., Tomographywith grating interferometers at low-brilliance sources, Sep. 2006,Proc. of SPIE: Developments in X-Ray Tomography, vol. 6318, p. 63180S-6,63180S-7.*

(Continued)

*Primary Examiner* — Glen Kao

(57) ABSTRACT

An X-ray radiography system for differential phase contrast imaging of an object under investigation by phase-stepping is provided. The X-ray radiography has an X-ray emitter for generating a beam path of quasi-coherent X-ray radiation, an X-ray image detector with pixels arranged in a matrix, and a diffraction or phase grating, in which the X-ray emitter has an X-ray tube with a cathode and an anode. The X-ray tube is constructed in such a way that an electron ray beam originating from the cathode is associated with focusing electronics which produce, from electrons which are incident on an anode, at least one linear-shaped electron fan beam.

5 Claims, 2 Drawing Sheets

(51) Int. Cl.
*H01J 35/14* (2006.01)
*G21K 1/06* (2006.01)

(56) References Cited

U.S. PATENT DOCUMENTS

| | | | |
|---|---|---|---|
| 2010/0074392 A1* | 3/2010 | Behling et al. | 378/4 |
| 2010/0091947 A1* | 4/2010 | Niu | A61B 6/484 378/63 |
| 2010/0133446 A1* | 6/2010 | Balakin | 250/397 |
| 2010/0246765 A1* | 9/2010 | Murakoshi et al. | 378/62 |
| 2011/0255667 A1* | 10/2011 | Lemaitre | H01J 35/06 378/113 |

OTHER PUBLICATIONS

Martin Spahn, Volker Heer & Rudolf Freytag; "Flachbilddetektoren in der Röntgendiagnostik", Der Radiologe, vol. 43 (2003), pp. 340-350; 2003; DE.

Pfeiffer, Franz et al., Phase retrieval and differential phase-contrast imaging with low-brilliance X-ray sources; Nature Physics 265, published online Mar. 26, 2006; Nature Publishing Group; pp. 1-4; doi:10.1038/nphys265.

\* cited by examiner

X-RAY RADIOGRAPHY SYSTEM FOR DIFFERENTIAL PHASE CONTRAST IMAGING OF AN OBJECT UNDER INVESTIGATION USING PHASE-STEPPING

CROSS REFERENCE TO RELATED APPLICATIONS

This application claims priority to German application No. 10 2013 214 393.1 DE filed Jul. 23, 2013, the entire content of which is hereby incorporated herein by reference.

FIELD OF INVENTION

The invention relates to an X-ray radiography system for differential phase contrast imaging of an object under investigation by means of phase-stepping, with an X-ray emitter for generating a beam path of quasi-coherent X-ray radiation, an X-ray image detector with pixels arranged in a matrix, and a diffraction or phase grating, in which the X-ray emitter has an X-ray tube with a cathode and an anode.

BACKGROUND OF INVENTION

Grating-based phase contrast imaging (PCI) is a relatively new imaging method by which, instead of an X-ray absorption image, measurement data is recorded which makes it possible to obtain in parallel both an absorption-based X-ray image, a differential phase image and a dark field image. From the data in the two additional images, further information can be obtained which can, for example, be used in a clinical diagnosis.

A requirement for grating-based phase contrast imaging is local coherence of the X-ray radiation, at least in one direction.

A further technological bottleneck is that the interference pattern which is to be recorded normally has a smaller periodic resolution than that which can be resolved by standard X-ray image detectors. The standard solution to this is to use a so-called phase-stepping technique, which will be explained in more detail below by reference to FIG. 2. With this, an analyzer grating $G_2$ with the periodicity of the undisturbed interference pattern is set up in front of the X-ray image detector, and is displaced relative to the object and the X-ray image detector, where the magnitude of the displacement is less than one period of the grating. From three or more one-shot recordings, the interference pattern can then be reconstructed.

For differential phase contrast imaging (PCI), it is usual to insert three gratings in the beam path from the source of the X-ray beam. The article "Phase retrieval and differential phase-contrast imaging with low-brilliance X-ray sources" by Franz Pfeiffer et al., which appeared in Nature Physics 2 (2006), pages 258 to 261, describes an example of this type of PCI, which will be explained in more detail below.

The wave nature of particles such as X-ray quanta permits phenomena like diffraction and reflection to be described with the help of the complex refractive index $$n = 1 - \delta + i\beta.$$

Here, the imaginary component $\beta$ describes the absorption, on which is based today's clinical X-ray imaging, such as for example computed tomography, angiography, radiography, fluoroscopy or mammography, and the real component $\delta$ describes the phase shift which is used in differential phase imaging.

From DE 10 2010 018 715 A1, an X-ray radiography system is known in which, for the purpose of high-quality X-ray imaging, for the purpose of phase contrast imaging of an object under investigation use is made of an X-ray radiography system which has at least one X-ray emitter with a plurality of field emission X-ray sources for emitting coherent X-ray radiation, an X-ray image detector, a diffraction grating $G_1$ arranged between the object under investigation and the X-ray image detector, and another grating $G_2$ which is arranged between the diffraction grating $G_1$ and the X-ray image detector.

An X-ray recording system, with which differential phase contrast imaging of the type mentioned in the introduction can be carried out, is known for example from U.S. Pat. No. 7,500,784 B2, and this will be explained by reference to FIG. 1.

FIG. 1 shows the typical main features of an X-ray radiography system for an intervention suite with a C-arm 2, held by a stand 1 in the form of a six-axis industrial or articulated arm robot, attached to the ends of which are an X-ray radiation source, for example an X-ray emitter 3 with X-ray tubes and collimator, and an X-ray image detector 4 as the image recording unit.

Using, for example, the articulated arm robot known from U.S. Pat. No. 7,500,784 B2, which preferably has six axes of rotation and hence six degrees of freedom, the C-arm 2 can be moved to any desired position in space, for example by being turned about a center of rotation between the X-ray emitter 3 and the X-ray image detector 4. The inventive angiographic X-ray system 1 to 4 can, in particular, be rotated about centers of rotation and axes of rotation in the plane of the C-arm of the X-ray image detector 4, preferably about axes of rotation which pass through the mid-point of the X-ray image detector 4 and the mid-point of the X-ray image detector 4.

The familiar articulated arm robot has a basic frame which, for example, has a fixed mounting on the floor. To this is attached a carousel that can rotate about a first axis of rotation. Attached to the carousel so that it can pivot about a second axis of rotation is a robot swing arm, to which is affixed a robot arm which can rotate about a third axis of rotation. At the end of the robot arm is attached a robot hand which can rotate about a fourth axis of rotation. The robot hand has a fixing element for the C-arm 2, which can pivot about a fifth axis of rotation and can rotate about a sixth axis of rotation oriented at right angles to the fifth.

The implementation of the X-ray diagnostic facility is not dependent on an industrial robot. It is also possible to make use of the usual C-arm or mammography devices.

The X-ray image detector 4 can be a rectangular or square flat semiconductor detector, preferably manufactured from amorphous silicon (a-Si) or selenium (a-Se). However, use could also be made of integrating and possibly counting CMOS detectors.

In the beam path from the X-ray emitter 3 there is, on a table plate 5 of a patient positioning table, a patient 6 who is to be investigated as the object under investigation. Connected to the X-ray diagnostic facility is a system control unit 7 with an imaging system 8, which receives and processes the image signals from the X-ray image detector 4 (examples of the operating elements are not shown). The X-ray images can then be inspected on displays on a suspended monitor 9. The suspended monitor 9 can be held by means of a ceiling-mounted, longitudinally movable, pivotable, rotatable and height-adjustable carrier system 10 with a cross-arm and lowerable carrier arm.

Instead of the X-ray system illustrated by way of example in FIG. 1, with its stand 1 in the form of a six-axis industrial or articulated arm robot, the angiographic X-ray system could also have a normal ceiling or floor mounted holder for the C-arm 2.

Instead of the C-arm 2 illustrated by way of example, the angiographic X-ray system could also have separate ceiling and/or floor mounted holders for the X-ray emitter 3 and the X-ray image detector 4, which are, for example, rigidly coupled to each other electronically.

In today's known arrangements for clinical phase contrast imaging, use is made of conventional X-ray tubes, X-ray image detectors which are today available, such as for example those described by Martin Spahn in "Flachbilddetektoren in der Röntgendiagnostik" [Planar image detectors in X-ray diagnostics], Der Radiologe, Volume 43 (5-2003), pages 340 to 350, and three gratings, $G_0$, $G_1$ and $G_2$, as will be explained in more detail by reference to FIG. 2, which shows schematically a structure for a Talbot-Lau interferometer for differential phase contrast imaging, with extended tube focus, gratings $G_0$, $G_1$ and $G_2$ and a pixelated X-ray image detector.

For the purpose of producing coherent radiation, the X-ray beams 12 emerging from a tube focus 11 of the non-coherent X-ray emitter 3 pass through an absorption grating 13 ($G_0$) which effects local coherence, and through an object under investigation 14, for example the patient 6. The object under investigation 14 deflects the wave front of the X-ray beam 12 by phase shifting in a way that is made clear by the normal 15 to the wave front when there is no phase shift, i.e. with no object, and the normal 16 to the wave front with phase shifting. Following this, the phase-shifted wave front passes through a diffraction or phase grating 17 ($G_1$), which has a grating constant matched to the mean energy of the X-ray spectrum, for the purpose of producing interference lines (Talbot effect), and then in turn through an absorptive analyzer grating 18 ($G_2$) for reading out the interference pattern produced. The grating constant of the analyzer grating 18 is matched to that of the phase grating 17 and to the remaining geometry of the arrangement. The analyzer grating 18 is, for example, arranged at the first or nth Talbot interval. By so-called "phase-stepping", described below, together with the analyzer grating 18 ($G_2$), it is possible to detect relevant items of data from the interference pattern, using the X-ray image detector 4.

If the tube focus 11 of the X-ray radiation source is sufficiently small, and the radiation power generated is nevertheless sufficiently large, it may be possible to forgo the first grating $G_0$, the absorption grating 13, as would be the case for example if a plurality of field emission X-ray sources are provided as the X-ray emitter 3, as is known from DE 10 2010 018 715 A1 which has been described.

For each pixel of the X-ray image detector 4, the image data is now determined in that, by the phase stepping 19, which is indicated by an arrow, the analyzer grating 18 ($G_2$) is moved in several steps (k=1, K, where for example K=3 to 8) by an appropriate fraction of the grating constant, perpendicularly to the direction of radiation of the X-ray beams 12 and laterally relative to the arrangement of the grating structure, and the signal $S_k$ which arises for this configuration during the recording is measured in the pixel of the X-ray image detector 4, and by this means the interference pattern which arose is sampled. For each pixel, the parameters of a function (e.g. a sine function) which defines the modulation is then determined by a suitable fitting method, by a matching or compensation method applied to the signals $S_k$ measured in this way. The visibility, i.e. the normalized difference between the maximal and minimal signals (or more precisely: the amplitude normalized to the mean signal), is here a measure for characterizing the quality of a Talbot-Lau interferometer. It is defined as the contrast of the sampled modulation $$V = \frac{I_{max} - I_{min}}{I_{max} + I_{min}} = \frac{A}{\bar{I}}.$$

Further, in this equation A represents the amplitude and $\bar{I}$ the mean intensity. The visibility can take on values between zero and one, because all the variables are positive and $I_{max} > I_{min}$. In a real interferometer it is also the case that $I_{min} > 0$, so that the value of V meaningfully extends across the whole range. Minimal intensities greater than zero, and all non-ideal characteristics and defects of the interferometer, lead to a reduction in the visibility. A third item of data which can be defined by means of the visibility and is generated by this type of measurement is called the dark field. The dark field gives the ratio of the visibilities of measurements with an object and those without an object.

$$D = \frac{V_{obj}}{V_{ref}} = \frac{A_{obj} \cdot \bar{I}_{ref}}{A_{ref} \cdot \bar{I}_{obj}}.$$

From a comparison of certain derived quantities from the functions fitted for each pixel, once with and once without an object (or patient), it is then possible to produce three different images:
(i) an absorption image,
(ii) a differential phase contrast image (DPC) and
(iii) a dark-field image.

In the case of the known PCI imaging methods, use is currently made of either a microfocus X-ray tube, which of itself meets the required coherence conditions, or alternatively an absorption grating with the designation $G_0$, which splits up the array of X-ray beams, output from the anode of the X-ray tube, into lines of X-rays. Each of these lines taken on its own satisfies the coherence condition and is so positioned by its spacing from its neighboring lines that in the plane of the detector the interference images overlay each other constructively in conformity with the method according to Lau.

The disadvantage of this method is that a large proportion of the X-ray radiation generated is absorbed in the absorption grating $G_0$, because the ratio of the opening to absorptive material is ≤1.

SUMMARY OF INVENTION

The invention is based on the object of designing an X-ray radiography system of the type mentioned in the introduction such that it permits particularly simple phase contrast imaging, with real time capability, with a high resolution and alternative local coherence of the X-ray radiation.

For an X-ray radiography system of the type mentioned in the introduction, this object is achieved in accordance with the invention by the features specified in claim 1. Advantageous developments are specified in the dependent claims.

For an X-ray radiography system, the objective is inventively achieved by constructing the X-ray tube in such a way that an electron ray beam originating from the cathode is associated with focusing electronics which produce, from electrons incident on an anode, at least one linear-shaped electron fan beam.

The effect of this is that the absorption grating $G_0$ is no longer necessary, so that almost all of the X-ray radiation which is produced can be used for the imaging.

It is advantageous that the conventional phase stepping can be replaced by a magnetic deflection facility, associated with the linear-shaped electron fan beam, which varies the point of incidence of the electrons on the anode so that a mechanical movement of the analyzer grating $G_2$ is no longer necessary.

It has proved to be advantageous if the focusing electronics produce at least one linear set of electron fan beams from electrons incident on an anode.

In accordance with the invention, the spacing between the lines of the linear set of electron fan beams can be dimensioned so that it satisfies the Lau condition, the constructive overlaying of the interference patterns at the site of the image plane.

It is advantageous if the focusing electronics are constructed in such a way that the spacing between the lines in the linear set is changed by actuation of the focusing electronics.

In accordance with the invention, it is possible to carry out an equivalent phase stepping if the linear-shaped electron fan beams are moved perpendicularly to the direction of the lines.

BRIEF DESCRIPTION OF THE DRAWINGS

The invention is explained in more detail below by reference to the exemplary embodiments shown in the drawing. This shows.

DETAILED DESCRIPTION OF INVENTION

Figure 1:
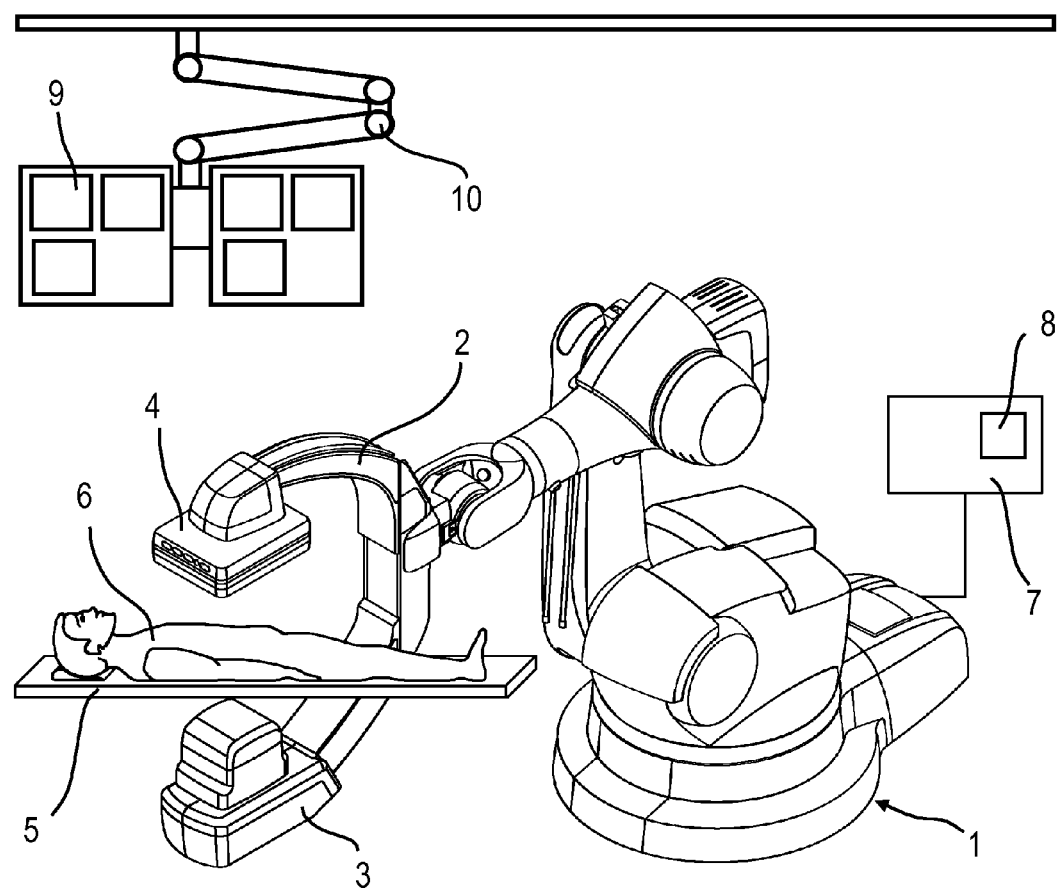
FIG. 1 a familiar C-arm angiography system in an interventional suite, with an industrial robot as the mounting fixture, FIG. 2 a schematic structure of a familiar Talbot-Lau interferometer for differential phase contrast imaging, with extended tube focus, three gratings $G_0$, $G_1$ and $G_2$ and a pixelated detector, and FIG. 3 a schematic structure of the electron beam system in an X-ray tube, with the inventive focusing of electrons onto the anode.
Figure 2:
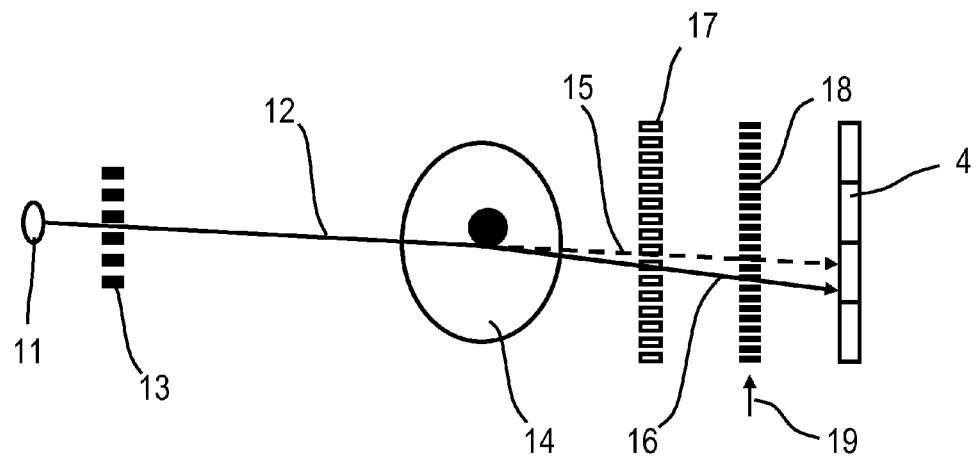
Figure 3:
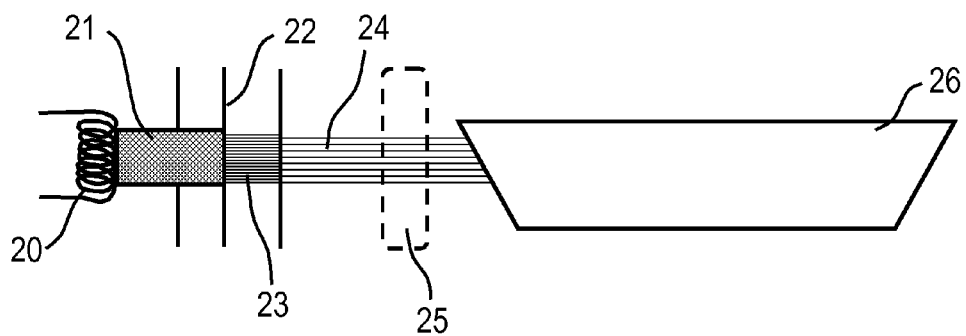

The X-ray tube of the X-ray emitter 3, equipped in accordance with the invention, is modified in such a way that electron ray beams 21 emerging from the cathode 20 are influenced by focusing electronics 22 in such a way as to form a first linear set 23 of linear-shaped electron fan beams. These can be yet further refined into a second linear set 24 of linear-shaped electron fan beams. A magnetic deflection device 25 can vary the points of incidence of the second linear set 24 on an anode 26, for example a stationary anode.

Within the X-ray tube of the X-ray emitter 3, the conventional focusing of the electrons onto the anode 26 is modified. The focusing electronics 22, which can consist of a lens and grating system, are constructed in such a way that the electrons are focused into lines each with a size, for example, of 4 μm×450 μm, so that the sets of lines 23 and 24 are formed. The spacing between the lines satisfies the Lau condition, the constructive overlaying of the interference patterns at the site of the image plane. Optionally, it is possible to alter the spacing by actuation of the focusing electronics 22.

Furthermore, the linear set 24 can be deflected by the magnetic field of the magnetic deflection device 25, as described for example in U.S. Pat. No. 8,284,894 B2. If the linear set 24 is moved perpendicularly to the direction of the lines, an equivalent phase stepping can be carried out by this means.

In the extreme case, the focus could consist of a single line (cf. DE 102 45 676 B4). The conventional phase stepping 19 can then be replaced by a suitable magnetic deflection of the focus.

It would also be possible to build up a chessboard pattern by electron focusing, thus producing coherence in two directions. It would then be possible to effect magnetic deflection in both directions or a "diagonal" movement.

The inventive construction of the X-ray tube of the X-ray emitter 3 enables almost all the X-ray radiation generated to be utilized for imaging purposes. Furthermore, the absorption grating $G_0$ is no longer necessary. A mechanical movement of the analyzer grating 18 ($G_2$) is also no longer required (phase stepping). It is sufficient to vary the magnetic field by means of the magnetic deflection device 25.

Using the inventive arrangement, one obtains an alternative local coherence of the X-ray radiation. Furthermore, there is a simplification of the PCI imaging method due to the replacement of the normal phase stepping 19 by the electrostatic and magnetic deflection of the electron ray beams 21 or the linear-shaped electron fan beams 23 and/or 24, as applicable.

The invention claimed is:

1. An X-ray radiography system for differential phase contrast imaging of an object under investigation by phase stepping, comprising:
   an X-ray emitter for generating electron ray beams;
   an X-ray image detector with pixels arranged in a matrix; and
   a diffraction or phase grating,
   wherein the X-ray emitter comprises an X-ray tube,
   wherein the X-ray tube comprises a cathode and an anode, and
   wherein the X-ray tube further comprises focusing electronics,
   wherein the electron ray beams emitted from the cathode are influenced by the focusing electronics to produce a first set of linear-shaped electron fan beams and a second set of further refined linear-shaped electron fan beams,
   wherein the second set of the further refined linear-shaped electron fan beams are incident on the anode, and
   wherein a spacing between lines of the first set of the linear-shaped electron fan beams and the second set of the further refined linear-shaped electron fan beams is changed by actuation of the focusing electronics.

2. The X-ray radiography system as claimed in claim 1, wherein the diffraction or phase grating is arranged between the object and the X-ray image detector, and wherein an analyzer grating is associated with the diffraction or phase grating.

3. The X-ray radiography system as claimed in claim 1, further comprising a magnetic deflection device which varies points of incidence of the second set of the further refined linear-shaped electron fan beams on the anode.

4. The X-ray radiography system as claimed in claim 1, wherein the spacing between the lines of the first set of the linear-shaped electron fan beams and the second set of the further refined linear-shaped electron fan beams is dimensioned in such a way that it satisfies Lau condition, a constructive overlaying of an interference pattern at a site of an image plane.

5. The X-ray radiography system as claimed in claim 1, wherein the lines of the second set of the further refined linear-shaped electron fan beams are moved perpendicularly to a direction of the lines.

\* \* \* \* \*